US006756496B1

(12) United States Patent
Froehler et al.

(10) Patent No.: US 6,756,496 B1
(45) Date of Patent: Jun. 29, 2004

(54) NUCLEOSIDE HYDROGEN PHOSPHONODITHIOATE DIESTERS AND ACTIVATED PHOSPHONODITHIOATE ANALOGUES

(75) Inventors: Brian C. Froehler, Belmont, CA (US); Chris A. Buhr, Daly City, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 08/972,998

(22) Filed: Nov. 19, 1997

Related U.S. Application Data

(60) Continuation of application No. 08/688,480, filed on Jul. 30, 1996, now abandoned, which is a division of application No. 08/391,338, filed on Feb. 21, 1995, now Pat. No. 5,565,555, which is a continuation of application No. 08/028,654, filed on Mar. 9, 1993, now abandoned, which is a division of application No. 07/248,517, filed on Sep. 23, 1988, now Pat. No. 5,194,599.

(51) Int. Cl.$^7$ .............................................. C07H 19/04
(52) U.S. Cl. .................. 536/26.6; 536/26.7; 536/26.74; 536/26.8; 536/26.9
(58) Field of Search .............................. 536/26.6, 26.7, 536/26.24, 26.8, 26.9

(56) References Cited

U.S. PATENT DOCUMENTS

| | | | | |
|---|---|---|---|---|
| 3,155,708 A | * | 11/1964 | Chupp et al. .................. 558/89 |
| 3,155,709 A | * | 11/1964 | Newallis et al. ............... 558/89 |
| 3,687,808 A | * | 8/1972 | Merigan, Jr. et al. ....... 435/91.3 |
| 4,024,049 A | * | 5/1977 | Shell et al. ............. 208/48 AA |
| 4,458,066 A | * | 7/1984 | Caruther et al. .......... 536/25.34 |
| 4,500,707 A | * | 2/1985 | Caruthers et al. ......... 536/25.34 |
| 5,194,599 A | * | 3/1993 | Froehler et al. ............ 536/26.7 |
| 5,565,555 A | * | 10/1996 | Froehler et al. .......... 536/26.22 |

FOREIGN PATENT DOCUMENTS

| | | |
|---|---|---|
| DE | 28 22 113 | 6/1979 |
| DE | 2822113 B1 * | 6/1979 |
| DE | 2822113 * | 6/1979 |
| EP | 0.219.342 A2 | 10/1986 |
| EP | 0219342 * | 10/1986 |
| EP | 0219342 A2 * | 10/1986 |
| EP | 0333489 A2 * | 9/1989 |
| EP | 0333489 * | 9/1989 |
| EP | 0506242 A1 * | 9/1992 |
| EP | 0506242 * | 9/1992 |
| WO | WO 89 /11486 | 11/1989 |
| WO | W O 89/11486 A1 * | 11/1989 |
| WO | 8911486 * | 11/1989 |
| WO | W0 90 12022 | 10/1990 |
| WO | W O 90/12022 A1 * | 10/1990 |
| WO | 9012022 * | 10/1990 |

OTHER PUBLICATIONS

Dahl et al. (I), "A Highly Reactive, Odourless Substitute for Thiophenol/Triethylamine as a Deprotection Reagent in the Synthesis of Oligonucleotides and their Analogues," *Acta Chim. Scand.*, 44, 639–641 (1990).*

Caruthers et al. (III), "Chemical and Biochemical Studies with Dithioate DNA," *Nucleosides & Nucleotides*, 10(1–3), 47–59 (1991).*

Stec et al. (II), "Novel Route to Oligo(deoxyribonucleoside Phosphorothioates). Stereocontrolled Synthesis of P–chiral Oligo(deoxyribonucleoside Phosphorothioates)," *Nucleic Acids Research*, 19(21), 5883–5888 (1991).*

Dahl et al. (II), "Deoxynucleoside Phosphorothioates. Preparation by a Triester Method," *Tetrahedron Letters*, 31(24), 3489–3492 (1990).*

Yau et al., "Synthesis of Dinucleoside and Dinucleotide Phosphorothioates via a Phosphotriester Approach," *Tetrahedron Letters*, 31(14), 1953–1956 (1990).*

Stec et al. (III), "Novel Method of Synthesis of Oligo(deoxyribonucleoside Phosphorothioates)," *Nucleic Acids Research Symposium Series*, vol 25, Oxford University Press, 1991, pp. 171–172.*

T. Greene, "Protection for the Hydroxyl Group Including 1,2– and 1,3– Diols," Ch. 2 in *Protective Groups in Organic Chemistry*, John Wiley & Sons, New York, 1981, pp. 10–86.*

Al'fonsov et al.(I), "Acetyl Phosphinothioates: Synthesis and Some Reactions," *Zu. Obshch. Khim.*, 55(10), 2203–2208 (1985).*

Al'fonsov et al. (II), "Phosphorylation of Thioacetic Acid with $P^{III}$ Acid Chlorides," *Zu. Obshch. Khim.*, 55(4), 932–933 (1985).*

Al'fonsov et al. (III), "Thioacetimidoylphosphites. Synthesis and Reactions with Protic Reagents," *Zu. Obshch. Khim.*, 55(3), 559–562 (1985).*

Andreev et al., "Organylphosphonic Acid Anhydrides and Their Thio Analogs," *Zh. Obshch. Khim.*, 52(8), 1785–1792 (1982).*

(List continued on next page.)

*Primary Examiner*—James O. Wilson
*Assistant Examiner*—L. Eric Crane
(74) *Attorney, Agent, or Firm*—Woodcock Washburn LLP

(57) ABSTRACT

Novel hydrogen-phosphonodithioate compositions are provided which are particularly useful for forming internucleotide and internucleoside linkages in oligonucleosides or oligonucleotides. The oligonucleotides and analogs thereof made by using the hydrogen-phosphonodithioate compositions may be therapeutically useful as antiviral and anticancer agents and may have other therapeutic or diagnostic uses. A method for making the hydrogen-phosphonodithioates is provided as well as a method for converting same to an activated intermediate for substitution on the phosphorus atom.

13 Claims, No Drawings

OTHER PUBLICATIONS

Brill et al., "Synthesis of Dinucleoside Phosphorothioates via Thioamidites," *Tetrahedron Letters, 29*, 5517–5520 (1988).*

Burilov et al., "S–Phosphorylated P(III) Derivatives," *Zu. Obshch. Khim., 55*(10), 2401 (1985).*

Dahl et al. (III), "Tetravalent Phosphorus Acids," *Organophosphorus Chemistry, 18*, 104–133 (1987).*

Eckstein, "Phosphorothioate Analogues of Nucleotides," *Angew. Chem. Intl. Ed., 22*(6), 423–506 (1983).*

Froehler et al. (III), "Phosphorothioate Analogues of DNA: Synthesis and Thermal Stability of Heteroduplexes," *Nucleic Acids Research, 16*(11), 1231–1239 (1988).*

Froehler et al. (IV), "Nucleoside H–Phosphonates: Valuable Intermediates in the Synthesis of Deoxyoligonucleotides," *Tetrahedron Letters, 4*, 469–472 (1986).*

Froehler et al. (V), "Synthesis fo DNA Via Deoxynucleoside H–Phosphonate Intermediates," *Nucleic Acids Research, 14*, 5399–5407 (1984).*

Gilbert et al., "Electron Spin Resonance Studies of the Photolysis and Radiolysis of O, O'–Dialkyl Hydrogen Phosphorodithioates [$(RO)_2P(S)SH$], Their Salts, Corresponding Disulfides, and Related Compounds," *J. Chem. Soc., Perkin Transactions I*, pp. 629–639 (1984).*

Gish et al., "DNA and RNA Sequence Determination Based on Phosphorothioate Chemistry," *Science, 240*, 1520–1522 (1988).*

Grandas et al., "Synthesis of Deoxycytidine Oligomers Containing Phosphorodithioate Linkages," *Tetrahedron Letters, 30*, 543–546 (1989).*

Grishina et al., "Synthesis of O–Sulfolanyl–3–alkyldithio–phosphonic Acids and Some Derivatives Thereof," *Zu. Obshch. Khim., 45*(4), 731–733 (1975).*

Marcus–Sekura et al., "Comparative Inhibition of Chloramphenicol Acetyltransferease Gene Expression by Antisense Oligonucleotide Analogues Having Alkyl Phosphotriester, Methylphosphonate and Phosphorothioate Linkages," *Nucleic Acids Research, 15*, 5749–5763 (1987).*

Matsukura et al., "Phosphorothioate Analogs of Oligodeoxynucleotides: Inhibitors of Replication and Cytopathic Effects of Human Immunodeficiency Virus," *Proc. National Academy Science USA, 84*, 7706–7710 (1987).*

Nielsen et al., "Synthesis and Characterization of Dinucleoside Phosphorodithioates," *Tetrahedron Letters, 29*(24), 2911–2914 (1988).*

Porritt et al., "Nucleoside Phosphonodithioates as Intermediates in the Preparation of Dinucleoside Phosphorodithioates and Phosphorothioates," *Tetrahedron Letters, 30*(35), 4713–4716 (1989).*

Smith et al., "Antiviral Effect of an Oligo(nucleoside methylphosphonate) Complementary to the Splice Junction of Herpes Simplex Virus Type 1 Immediate Early Pro–RNAs 4 and 5," *Proc. National Academy Science USA, 83*, 2787–2791 (1986).*

Stawinski et al., Nucleoside H–Phosphonates. X. Studies on Nucleoside Hydrogenphosphonothioate Diester Synthesis, *Tetrahedron Letters, 30*(16), 2157–2160 (1989).*

Voss et al., "Schwefelung von Harnstoffen mit $P_4S_{10}$," *J. Liebigs Ann. Chemie, 746*, 92–101 (1971).*

Al'fonsov et al, "Acetyl Phosphinothoites: Synthesis and Some Reactions," Zu Obshch Khim 55(10):2203–2208 (1985).

Al'fonsov et al, "Phosphorylation of thioacetic acid with p'" acid clorides, Zu Obshch Khim 55(4):932–3 (1985).

Al'fonsov et al., "Thioacetimidoylphosphites. Synthesis and reactions with protic reagents," Zu Obshch Khim 55(3):559–562 (1985).

Andreev et al., "Organylphosphonic acid anhydrides and their thio analogs," CHEM AB 97(25):216328p (1982).

Brill et al., "Synthesis of Dinucleoside Phosphorodithioates via Thioamidites," TET LETT 29:5517–5520 (1988).

Burilov et al, "S–Phosphorylated P(III) Derivatives," Zu Obshch Khim 55(10):2401 (1985).

Dahl, O., "Tetravalent Phosphorus Acids," ORGANOPH CHEM 18:104–133 (1987).

Eckstein, F., "Phosphorothioate Analogues of Nucleotides," Angew Chem Int Ed 22(6):423–506 (1983).

Froehler et al, "Phosphoramidate analogues of DNA: synthesis and thermal stability of heteroduplexes," Nuc Acids Res 16(11):1231–1239 (1988).

Froehler et al., "Nucleoside H–Phosphonates: Valuable Intermediates in the Synthesis of Deoxyoligonucleotides," TET LETT 4:469–472 (1986).

Froehler et al., "Synthesis of DNA via deoxynucleoside H–phosphonate intermediates," Nuc Acids Res 14:5399–5407 (1986).

Gilbert et al, "Electron Spin Resonance Studies of the Photolysis and Radiolysis of 0,0'–Dialkyl Hydrogen Phosphorodithioates [$(RO)2P(S)SH$], their Salts, Corresponding Disulphides, and Related Compounds," J Chem Soc Perkin Trans I 629–639 (1984).

Gish et al, "DNA and RNA Sequence Determination Based on Phosphorothioate Chemistry," Science 240:1520–1522 (1988).

Grishina et al, "Synthesis of O–sulfolanyl–3–alkyldithio–phosphonic acids and some derivatives thereof," Zu Obshch Khim 45(4):731–3 (1975).

Matsukura et al., "Phosphorothioate analogs of oligodeoxynucleotides: Inhibitors of replication and cytopathic effects of human immunodeficiency virus," Proc Natl Acad Sci 84:7706–7710 (1987).

Nielsen et al, "Synthesis and Characterization of dinucleoside phosphorodithioates," Tet Lett 29(24):2911–2914 (1988).

Porritt et al, "Nucleoside Phosphonodithioate as intermediates in the preparation of dinucleoside phosphorodithioates and phosphorothioates," Tet Lett 30(35):4713–4716 (1989).

Smith et al., "Antiviral effect of an oligo(nucleoside methylphosphonate) complementary to the splice junction of herpes simplex virus type 1 immediate early pre–mRNAs 4 and 5," Proc Natl Acad Sci 83:2787–2791 (1986).

Stawinski et al, "Nucleoside H–phosphonates. X. Studies on nucleoside hydrogenphosphonothioate diester synthesis," Tet Lett 30(16):2157–2160 (1989).

Voss, J., "Schwefelung von Harnstoffen mit P4S10," Liebigs Ann Chem 746:92–101 (1971).

* cited by examiner

NUCLEOSIDE HYDROGEN PHOSPHONODITHIOATE DIESTERS AND ACTIVATED PHOSPHONODITHIOATE ANALOGUES

This is a continuation of application(s) Ser. No. 08/688,480, which was filed on Jul. 30, 1996 now abandoned which is a Divisional application of Ser. No. 08/391,338, filed on Feb. 21, 1995, now U.S. Pat. No. 5,565,555; which is a Continuation application of Ser. No. 08/028,654, filed on Mar. 9, 1993, now abandoned; which is a Divisional application of Ser. No. 07/248,517, filed on Sep. 23, 1988, now U.S. Pat. No. 5,194,599.

The present invention is directed to novel hydrogen phosphonodithioates, and in particular to nucleosides, deoxynucleosides, nucleotides and deoxynucleotides containing novel hydrogen phosphonodithioate groups.

BACKGROUND OF INVENTION

Internucleotide phosphate analogs have recently gained interest as having uses in and of themselves, other than for making recombinant DNA for application in genetic engineering techniques. For example, methanephosphonate linked deoxyoligonucleotides inhibit viral replication in mammalian cells (Smith, C. C., et al., *Proc. Natl. Acad. Sci. USA* 83, 2787–2791 (1986)) and some phosphorothioates have been shown to have anti-HIV activity (Matsukura, et al., *Proc. Natl. Acad. Sci. USA* 84, 7706–7710 (1987)). Internucleotide phosphate analog linkages, such as the phosphoramidate linkages, are useful as an attachment for reporter groups, intercalating agents and cross-linking agents. Such linkages also can be resistant to certain nucleases which would otherwise act upon naturally-occurring phosphate internucleotide linkages. Moreover, the modification of the phosphorus-containing internucleotide linkages has been shown to affect gene expression (Marcus-Sekura, et al., *Nucl. Acids Res.* 15, 5749–5763 (1987)). Therefore, there is a continuing interest in phosphate analogs for all of these utilities, as well as for use in synthesizing sequence-defined oligonucleotides and analogs thereof.

SUMMARY OF THE INVENTION

The present invention provides novel and useful hydrogen phosphonodithioates of the formula I:

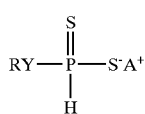

in general wherein each R is independently a substituted or unsubstituted hydrocarbyl group, or substituted or unsubstituted hydrocarbyl group containing one or more heteroatoms; Y is O, S, —NH— or —NR—; and $A^+$ is a cation. By the term hydrocarbyl it is meant any group which contains at least the elements hydrogen and carbon. This term is not intended to be limited to groups which contain only. hydrogen and carbon.

Particularly preferred compounds are those wherein the R group is a nucleoside, nucleotide, deoxynucleoside, .deoxynucleotide or any protected or modified derivative of any of those groups. The most preferred class comprises those compounds wherein Y is oxygen. The nucleosides, nucleotides, deoxynucleosides or deoxynucleotides may be protected at any functional site on the molecule.

It will be appreciated that as used herein the terms "nucleosides" and "nucleotides" will include those moieties which contain not only the known purine and pyrimidine bases, but also bases which have been modified. Such modifications include methylated purines or pyrimidines, acylated purines or pyrimidines, and the like.

Modified nucleosides or nucleotides will also include modifications on the sugar moiety, for example, wherein one or more of the hydroxyl groups are replaced with halogen, or functionalized as ethers, etc.

Examples of modified nucleosides or nucleotides which may comprise R in formula I include, but are not limited to:

| | |
|---|---|
| 2-aminoadenosine | deoxy-2-aminoadenosine |
| 5-bromouridine | deoxy-5-bromouridine |
| 5-chlorouridine | deoxy-5-chlorouridine |
| 5-fluorouridine | deoxy-5-fluorouridine |
| 5-iodouridine | deoxy-5-iodouridine |
| 5-methyluridine | (deoxy-5-methyluridine is the same as thymidine) |
| inosine | deoxy-inosine |
| xanthosine | deoxy-xanthosine |

In general, the compounds according to the present invention are useful in oligonucleotide synthesis to generate analogous internucleotide linkages. The nucleotide (or nucleoside) monomers and oligomers may also themselves have antiviral activity, anticancer utility, or other therapeutic utility, and may also have diagnostic, pesticidal, agricultural, animal health care, or plant health care uses. In particular, the compounds of the invention are useful research reagents for forming internucleotide linkages. A particularly preferred use of the compounds of the present invention is to form internucleotide hydrogen phosphonothioate linkages, which can, in turn, be converted to other phosphothioate linkages.

DESCRIPTION OF PREFERRED EMBODIMENT

In general, and as defined in more detail hereinbelow, the compounds according to the present invention include those in which R may be alkyl, alkenyl, cycloalkyl, cycloalkenyl, aryl, aralkyl, substituted alkyl, substituted alkenyl, substituted cycloalkyl, substituted cycloalkenyl, substituted aryl, or substituted aralkyl, including a protected or unprotected nucleoside, nucleotide, deoxynucleoside or deoxynucleotide.

As described in more detail hereinbelow, the compounds according to the present invention may be prepared by treatment of an acidic azole with phosphorus trihalide to form a reactive intermediate which can be treated directly with the compound ROH, RSH, $RNH_2$ or RRNH, wherein R is as described herein. Subsequent treatment with hydrogen sulfide, followed by a base, results in compounds of the present invention. It will be appreciated that 1,2,4-triazole, tetrazoles, or other reactants may be utilized in the synthesis provided they form an intermediate upon reaction with phosphorus trihalide which, in turn, undergoes the desired addition of the ROH, RSH, $RNH_2$ or RRNH utilized in the synthesis.

In a preferred embodiment of the present invention, the compounds of the invention may be made into activated intermediates by conversion of one of the sulfur atoms to a suitable leaving group, under appropriate conditions, such as a thioalkanoate group,

This activated intermediate is useful for conversion to other useful compounds, such as by reaction with a nucleoside or nucleotide to form hydrogen phosphonothioate ester-linked nucleosides or nucleotides.

The compounds according to the present invention may be made in general in situ by treatment of one equivalent of a phosphorus trihalide, preferably phosphorus trichloride, in a suitable solvent with an excess of a reactive acidic azole, such as 1,1,4-triazole, in 3 to 4 equivalent excess. Then an equivalent amount or less, of a suitable reagent, ROH, RSH, $RNH_2$ or RRNH, wherein R is as defined herein, can be added in the presence of a base. Then treatment with hydrogen sulfide followed by neutralization, such as with trialkyl ammonium bicarbonate, results in compounds according to the present invention, which can be isolated by chromatography, crystallization, distillation, and the like, by conventional procedures.

While generally the synthesis has been described utilizing 1,2,4-triazole, any other suitable acidic azole may be utilized in the synthesis, since the triazole does not appear in the final compound. Other azoles include, but are not limited to, for example, tetrazoles, and the like. Suitable solvents for the in situ reaction will depend, of course, on the solubility of the particular azole utilized in the initial reaction with the phosphorus trihalide, and upon the solubility of the reagent ROH, RSH, $RNH_2$ or RRNH.

Since R may contain one or more functional groups, these groups will be protected during the synthesis of the compounds according to the present invention, particularly if such functional groups are reactive with electrophilic phosphorus species or hydrogen sulfide under the reaction conditions of the synthesis. Conventional blocking groups may be utilized, such as those used for blocking hydroxyl, sulfhydryl, carboxyl and amino groups in chemical synthesis, particularly those groups used for blocking functionalities in peptide synthesis or oligonucleotide synthesis.

In a preferred embodiment of the present invention, R will be a nucleoside, nucleotide, deoxynucleoside or deoxynucleotide, which contains hydroxyl functionalities as well as amine functionalities in the basic side chains. Under the conditions of reactions for the synthesis of compounds according to the present invention described above, typically the 5' or 3' hydroxyl group of the ribonucleoside will be protected by a hydroxyl protecting group, preferably the dimethoxytrityl group. The reactive amine groups on the basic side chains may be protected by an amine protecting group, such as an acyl group or amidine. It will be recognized by those of ordinary skill in the art that many other protecting groups may be utilized which will serve to protect the appropriate functionalities under the conditions of the synthesis of the present invention. Some, but not all, protecting groups and the conditions for their use are shown, for example, in Greene, T. W., *Protective Groups in Organic Synthesis,* Wiley & Sons, N.Y., 1981.

The cation $A^+$ may be any cation, particularly one which serves as a counterion to the neutralizing agent in the final step of the synthesis of compounds of Formula I. In the final step of the above-described synthesis, excess hydrogen sulfide and the thioacidic proton on the phosphonodithioate group are neutralized by addition of a reagent such as bicarbonate. The counterion to the bicarbonate will form the initial $A^+$ moiety in the compound of the present invention. A particularly preferred neutralizing agent for use in the present synthesis is a trialkylammonium bicarbonate whereby the trialkylammonium ion comprises the $A^+$ counterion in the resulting compound. A particularly preferred salt for the neutralization reaction is triethylammonium bicarbonate.

It will be appreciated that the moiety $A^+$ is a cation which results in treatment of the thioacid made in situ by treatment with hydrogen sulfide. In some instances a cation $A^+$ other than the counterion to the acid used for the neutralization reaction may be desired. To prepare a different salt, the original salt product may be dissolved in an organic solvent, such as dichloromethane, then extracted by contact with an aqueous phase containing the desired cation $A^+$. Examples of other cations include, but are not limited to:

1,5-diazabicyclo[4.3.0]non-5-ene ammonium (DBN)

1,4-diazabicyclo[2.2.2]octane ammonium (DABCO)

1,8-diazabicyclo[5.4.0]undec-7-ene ammonium (DBU)

tetrabutylammonium tributytlammonium triethylammonium diisopropylethylammonium 1,8-bis-dimethylaminonaphthalene ammonium benzyltrimethylammonium benzyltriethylammonium A preferred cation is the DBU cation.

The group R of the compounds according to the present invention may be linear or branched alkyl containing 1 to 20 carbon atoms, such as methyl, propyl, isopropyl, n-butyl, isobutyl, t-butyl, isopentyl, neopentyl, n-octyl, n-dodecyl, and the like. The group R may also be a linear or branched alkenyl group containing 1 to 20 carbon atoms such as isopropenyl, 1,4-butadienyl, 3-octenyl, and the like.

The group R may also be cycloalkyl or cycloalkenyl containing 3 to 20 carbon atoms, including, but not limited to, cyclopropyl, cyclopentyl, cyclohexyl, cyclooctyl, cyclopentenyl, cyclohexenyl, and the like.

The group R may be an aryl group containing 6 to 18 carbon atoms such as phenyl, anthracyl, naphthyl, azulyl, phenanthryl, and the like.

The R group may also be an aralkyl group containing about 7 to 60 carbon atoms, including, but not limited to, benzyl, 4-phenylbutyl, and the like.

The alkyl, alkenyl, cycloalkyl, cycloalkenyl, aryl or aralkyl groups may further contain one or more heteroatoms such as oxygen, nitrogen, sulfur, silicon, in the form of functionalities including, but not limited to, ethers, thioates, heterocyclics, carboxylic acids, esters, ketones, and the like.

Additionally, the alkyl, alkenyl, cycloalkyl, cycloalkenyl, aryl, aralkyl groups optionally containing one or more heteroatoms may contain one or more substituents. Typical substituents include hydroxyl, nitro, sulfhydryl, cyano, alkylcarbonyl, alkoxyl, halo, alkylthio, alkylcarboxyl, amino (including primary, secondary, tertiary or quaternary) group. For example, substituents may be selected from the group consisting of —OH, —$NO_2$, —SH, —CN, O=CR", —OR', —X, —SR' and —$CO_2$R" wherein X is halo, R' is a removable protecting group or phosphate group; and R" is hydrogen or a linear, branched or cycloalkyl containing 1 to 10 carbon atoms, aryl containing 6 to 10 carbon atoms or aralkyl containing 7 to 20 carbon atoms, optionally containing halo or hydroxy substituents.

A preferred class of compounds are those wherein R is of the formula IIA or IIB:

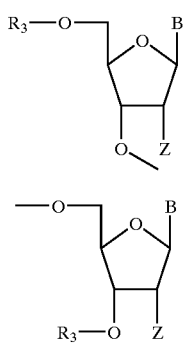

IIA

IIB wherein B is a protected or unprotected nucleoside base; Z is hydrogen, —OH, —OR$_3$ or alkyl containing 1 to 6 carbon atoms, and each R$_3$ is independently a phosphorus-containing group, heteroatom-containing alkyl, haloalkyl or alkyl of 1–10 carbon atoms, protecting group, aryl or substituted aryl wherein the aryl nucleus contains 6–10 carbon atoms, or aralkyl of 7–20 carbon atoms. For example, R$_3$ may be the phosphorus-containing group —CH$_2$—(P)— wherein (P) is phosphorus in any of its valence states. The compounds according to the formula IIA and IIB include, but are not limited to, adenosinyl, guanosinyl, cytidinyl, uridinyl, deoxyadenosinyl, deoxyguanosinyl, deoxycytidinyl, thymidinyl, 2'-methyl-deoxyadenosinyl, 2'-methyl-deoxyguanosinyl, 2'-methyl-deoxycytidinyl and 2'-methyl-thymidinyl. It will be appreciated that a unique stereochemistry is not to be inferred by the formulas IIA or IIB. The formulas are intended to be generic not only to the naturally-occurring stereochemistry (including α and β anomeric configurations at the 1'-position) but also to any and all combinations of stereochemical configurations of the chiral sites.

It will be realized that blocking groups may be required on one or more functional groups during the synthesis of compounds according to the present invention. These blocking groups, if required, may be removed by procedures recognized in the art, for example by using mild bases, such as ammonium hydroxide, at room temperature or at elevated temperatures. There are numerous blocking groups for different functionalities which are known in the art which can be removed under similar conditions, such as, blocking groups which are commonly used in peptide synthesis. Other blocking groups may be removed in stepwise manner. For example, esters which may be used to block carboxyl functionalities may be removed by treatment with ammonium hydroxide at approximately room temperature (20° C.) and N-acyl blocking groups, such as acetyl, benzoyl, and the like, may be removed by warming an ammonium hydroxide-containing solution to about 50° C.

Removal of hydroxyl blocking groups such as dimethoxytrityl, trityl and the like may be accomplished by use of any suitable protic acid in a suitable solvent or a Lewis acid such as zinc bromide, aluminum chloride, boron trifluoride, titanium tetrachloride, nitromethane, tetrahydrofuran, or alcohols, under conditions known in the art.

As previously discussed, the compounds according to the present invention may have antiviral or anticancer activity or other therapeutic applications, as well as diagnostic, agricultural, animal health care, or plant health care uses. In a particularly preferred embodiment of the use of compounds according to the present invention, compounds of the formula I may be activated for substitution on the phosphorus atom by treatment with a reagent which converts one of the sulfur atoms to a suitable leaving group, thus activating the phosphorus atom. A particularly preferred reagent is an acylating agent, such as pivaloyl chloride, which acylates one of the sulfur atoms to form the thioalkanoate leaving group

The phosphorus atom is thereby activated, and in this instance may be converted to other useful compounds, such as by reaction with a nucleoside or nucleotide having a free hydroxyl group to form a phosphothioate ester by displacement of the

leaving group.

Thus, it is another aspect of the present invention to provide novel compounds of the formula III

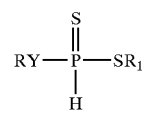

III wherein R is as defined hereinabove in connection with the formula I and —SR$_1$ is a leaving group under appropriate conditions of substitution at the phosphorous atom. The group R$_1$ may therefore be an acyl group such as pivaloyl, adamantyl, acetyl, benzoyl, p-methoxybenzoyl, or other suitable leaving group, such as a thioacyl, phosphoryl or thiophosphoryl group. A preferred acylating agent is an amide or acid halide, particularly an acid chloride, such as acetyl chloride. An acylating agent may also be, for example, an N-acyl azole, or any other reagent wherein the group R$_1$ is activated with a suitable leaving group. Other R$_1$ groups include

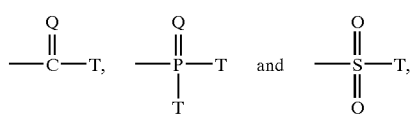

wherein Q is NR$_2$, oxygen or sulfur and T is alkyl of 1–10 carbon atoms, aryl or substituted aryl wherein the aryl nucleus contains 6 to 10 carbon atoms, aralkyl of 7–20 carbon atoms, —NR$_2$R$_2$, —SR$_2$, —OR$_2$; wherein each R$_2$ is independently hydrogen, alkyl of 1–10 carbon atoms, aryl or substituted aryl wherein the aryl nucleus contains 6–10 carbon atoms or aralkyl of 7–20 carbon Moms. It is realized that some R$_1$ groups, such as

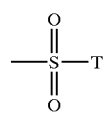

form transient compounds which may subsequently undergo intramolecular rearrangements involving the phosphorus nucleus, however, such transient compounds are deemed to be within the scope of the invention.

The activated compound of formula III above will react with another compound, preferably an unprotected hydroxyl group of a nucleoside or deoxynucleoside, in a suitable solvent, thereby forming a phosphothioate ester of the formula IV:

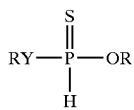

IV

It will be understood, of course, that under appropriate and well known conditions of substitution, the group $R_1S-$ must be a preferred leaving group over the substituent $RY-$ to obtain the desired product. Thus in the embodiment wherein the phosphorus atom is to undergo substitution by displacement of $R_1S-$, it is preferred that R in formula III not be another acyl group which would compete as a leaving group with $R_1S-$.

In order to assist in comprehension and understanding of the invention, the following examples are described, but are not intended to limit the scope of the present invention in any manner.

EXAMPLE 1

Preparation of Triethylammonium 5'-Dimethoxytrityl-3'-Thymidine-Hydrogen-Phosphonodithioate To a stirred mixture of 11.2 g (160 mmol) of 1,2,4-triazole, and 40.0 mL of N-methyl morpholine (360 mmol) in 200 mL of $CH_2Cl_2$ was added 20.0 mL (40.0 mmol) of a 2.0 M solution of $PCl_3$ in $CH_2Cl_2$ at room temperature over 5 min. After 30 min. the reaction was cooled between $-5-\!-10°$ C. (external). To this mixture was added a solution of 5.50 g (10.1 mmol) of 5'-dimethoxytrityl thymidine (dried by coevaporation from 100 mL of dry pyridine) in 40.0 mL of pyridine over 10 min. Stirring was continued for 10 minutes. Next, 250 mL of pyridine was cooled between $-15-\!-20°$ C. and saturated with $H_2S$. This solution was cannulated under argon to the previously prepared reaction mixture. After stirring for 1 h, the reaction mixture was poured onto 1400 mL of an ice cold 1.0 M aqueous triethylammonium bicarbonate (TEAB, pH 8.2) with stirring. After 15 min. the mixture was extracted with 3×500 mL of $CH_2Cl_2$. The combined organics were then washed with 2×500 mL of 1.0 M TEAB, dried ($NaSO_4$), filtered, and concentrated. The product was purified by flash chromatography using $CH_3CN:CH_2Cl_2$ 1:1 containing 0.5% triethylamine.(TEA) as eluant. This procedure afforded 2.73 g (36.4% yield) of the title product.

EXAMPLE 2

Preparation of 1.8-Diazabicyclo[5.4.0]Undec-7-Ene Salt of 5'-Dimethoxytrityl-3'-Thymidine H-Phosphonodithioate A solution of 2.73 g of triethylammonium 5'-dimethoxytrityl-3'-thymidine H-phosphonodithioate in 250 ml of $CH_2Cl_2$ was washed with 3×100 mL of an aqueous solution of 0.1 M DBU bicarbonate (pH=8.5), dried ($Na_2SO_4$), filtered, and concentrated affording the product as a colorless solid.

EXAMPLE 3

Preparation of Triethylammonium Deoxy-$N^4$-Benzoyl-5'-Dimethoxytrityl -3'-Cytidine-Hydrogen-Phosphonodithioate To a stirred mixture of 560 mg (8.1 mmol) of 1,2,4-triazole, and 2.00 mL of N-methyl morpholine (18 mmol) in 10 mL of $CH_2Cl_2$ was added 1.0 mL (2.0 mmol) of a 2.0 M solution of $PCl_3$ in $CH_2Cl_2$ at room temperature over 5 min. After 30 min. the reaction was cooled on an ice water bath. To this mixture was added a solution of 317 mg (0.500 mmol) of deoxy-$N^4$-benzoyl-5'-dimethoxytrityl cytidine (dried by coevaporation from dry pyridine) in 2.00 mL of pyridine over 5 min. Stirring was continued for 1 h. Next, 15 mL of pyridine was cooled at 0° C. and saturated with $H_2S$. This solution was cannulated under argon to the previously prepared reaction mixture. After stirring for 1 h, the reaction mixture was poured onto 70 mL of an ice cold 1.0 M aqueous triethylammonium bicarbonate (TEAB, pH 8.2) with stirring. After 15 min. the mixture was extracted with 2×60 mL of $CH_2Cl_2$. The combined organics were then washed with 2×50 mL of 1.0 TEAB, dried ($Na_2SO_4$), filtered and concentrated. The product was purified by flash chromatography using $CH_3CN:CH_2Cl_2$ 13:7 containing 0.5% triethylamine (TEA) as eluant. This procedure afforded 144 mg (34.6% yield) of the title product.

EXAMPLE 4

Preparation of Triethylammonium Deoxy-$N^6$-Benzoyl5'-Dimethoxytrityl-3'-Adenosine H-Phosphonodithioate To a stirred mixture of 560 mg (8.1 mmol) of 1,2,4-triazole, and 2.00 mL of N-methyl morpholine (18 mmol) in 10 mL of $CH_2Cl_2$ was added 1.0 mL (2.0 mmol) of a 2.0 M solution of $PCl_3$ in $CH_2Cl_2$ at room temperature over 5 min. After 30 min. the reaction was cooled on an ice water bath. To this mixture was added a solution of 329 mg (0.500 mmol) of deoxy-$N^6$-benzoyl-5'-dimethoxytrityl-3'-adenosine (dried by coevaporation from dry pyridine) in 2.00 mL of pyridine over 3 min. Stirring was continued for 20 min. Next, 20 mL of pyridine was cooled at 0° C. and saturated with $H_2S$. To this $H_2S$-pyridine solution was cannulated (under argon) the previously prepared triazolide reaction mixture at 0° C. After stirring for 15 min. the reaction mixture was poured onto 70 mL of an ice cold 1.0 M aqueous triethylammonium bicarbonate (TEAB, pH 8.2) with stirring. After 15 min. the mixture was extracted with 2×60 mL of $CH_2Cl_2$. The combined organics were then washed with 2×50 mL of 1.0 M TEAB, dried ($Na_2SO_4$), filtered, and concentrated. The product was purified by flash chromatography using $CH_3CN:CH_2Cl_2$ 6:4 containing 2.0% triethylamine (TEA) as eluant. This procedure afforded 122 mg (28.5% yield) of product.

EXAMPLE 5

Preparation of Triethylammonium Deoxy-$N^2$-Benzoyl-5'-Dimethoxytrityl-3'-Guanosine H-Phosphonodithioate To a stirred mixture of 560 mg (8.1 mmol) of 1,2,4-triazole, and 2.00 mL of N-methyl morpholine (18 mmol) in 10 mL of $CH_2Cl_2$ was added 1.0 mL (2.0 mmol) of a 2.0 M solution of $PCl_3$ in $CH_2Cl_2$ at room temperature over 5 min. After 30 min. the reaction was cooled on an ice water bath. To this mixture was added a solution of 320 mg (0.500 mmol) of deoxy-$N^2$-isobutyryl-5'-dimethoxytrityl-3'-guanosine (dried by coevaporation from dry pyridine) in 2.00 mL of pyridine over 2 min. Stirring was continued for 5 min. Next, 20 mL of pyridine was cooled at 0° C. and saturated with $H_2S$. To this $H_2S$-pyridine solution was cannulated (under argon) the previously prepared triazolide reaction mixture at 0° C. After stirring for 15 min. the reaction mixture was poured onto 70 mL of an ice cold 1.0

M aqueous triethylammonium bicarbonate (TEAB, pH 8.2) with stirring. After 15 min. the mixture was extracted with 2×60 mL of $CH_2Cl_2$. The combined organics were then washed with 2×50 mL of 1.0 M TEAB, dried ($Na_2SO_4$), filtered, and concentrated. The product was purified by flash chromatography using EtOAc: acetone: $H_2O$ 16:8:1 containing 2.0% triethylamine (TEA) as eluant. This procedure afforded 66.6 mg (15.9% yield) of product.

EXAMPLES 6 Through 17

By following essentially the same procedures shown above in Examples 1 and 2, various compounds of the formula I are made by substituting a different starting material for the protected nucleoside in a suitable solvent. The following compounds are respectively prepared as the triethylammonium salt:

O-isobutyl-hydroqen-phosphonodithioate
O-isopropenyl-hydrogen-phosphonodithioate
O-cyclohexyl-hydrogen-phosphonodithioate
O-(3,5-cyclohexadienyl-hydrogen-phosphonodithioate
O-(1'-naphthyl)-hydrogen-phosphonodithioate
O-(p-nitrobenzyl)-hydrogen-phosphonodithioate
O-(methoxymethyl)-hydrogen-phosphonodithioate
O-((3-dimethylamino)-butyl)-hydrogen-phosphonodithioate
O-(4-methoxy-2-fluoro-phenyl)-hydrogen-phosphonodithioate
O-(4'-N-methylpyridyl)-hydrogen phosphonodithioate
O-(n-butylthiobutyl)-hydrogen-phosphonodithioate
O-(N-benzoyl-1-carbazolyl)-hydrogen-phosphonodithioate Having described the specific embodiments of the invention, other modifications and variations will be apparent to those of ordinary skill in the art, which variations and modifications are intended to be within the scope of the present invention.

What is claimed is:
1. A compound of the formula

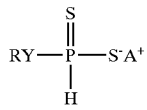

wherein Y is S, —NH— or —NR—;
$A^+$ is a cation; and R is a protected or unprotected nucleoside, nucleotide, modified nucleoside or modified nucleotide, or R is a protected or unprotected deoxynucleoside, deoxynucleotide, modified deoxynucleoside or modified deoxynucleotide.

2. The compound of claim 1 wherein R is protected or unprotected adenosinyl, guanosinyl, cytidinyl, uridinyl, 2-aminoadenosinyl, 5-bromouridinyl, 5-chlorourdinyl, 5-fluorouridinyl, 5-iodouridinyl, 5-methyluridinyl, inosinyl, xanthosinyl, deoxyadenosinyl, deoxyguanosinyl, deoxycytidinyl, thymidinyl, deoxy-2-aminoadenosinyl, deoxy-5-bromouridinyl, deoxy-5-chlorourdinyl, deoxy-5-fluorouridinyl, deoxy-5-iodouridinyl, deoxyinosinyl or deoxyxanthasinyl.

3. The compound of claim 1 wherein R is 5'-dimethoxytrityl-3'-(thymidinyl.

4. The compound of claim 1 wherein R is deoxy-$N^4$-benzoyl-5'-dimethoxytrityl-3'-cytidinyl.

5. The compound of claim 1 wherein R is deoxy-$N^6$-benzoyl-5'-dimethoxytrityl-3'-adenosinyl.

6. The compound of claim 1 wherein R is deoxy-$N^2$-isobutyryl-5'-dimethoxytrityl-3'-guanosinyl.

7. The compound of claim 1 wherein $A^+$ is 1,5-diazabicyclo[4.3.0]non-5-ene ammonium, 1-4-diazabicyclo[2.2.2]octane ammonium, 1,8-diazabicyclo[5.4.0]undec-7-ene ammonium, tetrabutylammonium, tributylammonium, triethylammonium, diisopropylethylammonium, 1,8-bisdimethylaminoaphthalene ammonium, benzyltrimethylammonium, or benzyltriethylammonium ion.

8. A compound according to claim 7 wherein $A^+$ is 1,8-diazabicyclo[5.4.0]undec-7-ene ammonium ion.

9. The compound of claim 1 wherein $A^+$ is 1,5-diazabicyclo[4.3.0]non-5-ene ammonium, 1,4-diazabicyclo[2.2.2]octane ammonium, 1,8-diazabicyclo[5.4.0]undec-7ene ammonium, tetrabutylammonium, tributylammonium, triethylammonium, diisopropylethylammonium, 1,8-bisdimethylaminonaphthalene ammonium, benzyltrimethylammonium, or benzyltriethylammonium ion.

10. A compound according to claim wherein $A^+$ is 1,8-diazabicyclo[5.4.0]undec-7ene ammonium ion.

11. The compound of claim 1 wherein R is a 2'-halo-$N^4$-benzoyl-5'-dimethoxytrityl-3'-cytidinyl.

12. The compound of claim 1 wherein R is a 2'-halo-$N^6$-benzoyl-5'-dimethoxytrityl-3'-adenosinyl.

13. The compound of claim 1 wherein R is a 2'-halo-$N^2$-isobutryl-5'-dimethoxytrityl-3'-guanosinyl.

* * * * *

UNITED STATES PATENT AND TRADEMARK OFFICE
CERTIFICATE OF CORRECTION

PATENT NO. : 6,756,496 B1
DATED : June 29, 2004
INVENTOR(S) : Brian C. Froehler et al.

It is certified that error appears in the above-identified patent and that said Letters Patent is hereby corrected as shown below:

Title page,
Item [56], References Cited, OTHER PUBLICATIONS, "Dahl et al." reference, please delete "Chim." and insert therefor -- Chem. --;

Column 10,
Line 5, please insert -- : -- after "unprotected";
Line 14, please delete "(";
Line 35, please insert -- - -- between "7" and "ene";
Line 40, please insert -- 9 -- between "claim" and "wherein";
Line 41, please insert -- - -- between "7" and "ene".

Signed and Sealed this

Fifth Day of April, 2005

JON W. DUDAS
*Director of the United States Patent and Trademark Office*